(12) United States Patent
Ahmad et al.

(10) Patent No.: US 8,985,108 B2
(45) Date of Patent: Mar. 24, 2015

(54) MECHANICAL VENTILATION MASK FIT STATUS INDICATION

(75) Inventors: Samir S. Ahmad, San Diego, CA (US); Leonardo Alberto Baloa Welzien, Lake Forest, CA (US); Enrico Brambilla, Irvine, CA (US); Lauren Cheney, San Marcos, CA (US); Iva Segalman, Irvine, CA (US); Simon Johnson, Carlsbad, CA (US)

(73) Assignee: Breathe Technologies, Inc., Irvine, CA (US)

( * ) Notice: Subject to any disclaimer, the term of this patent is extended or adjusted under 35 U.S.C. 154(b) by 375 days.

(21) Appl. No.: 13/441,607

(22) Filed: Apr. 6, 2012

(65) Prior Publication Data
US 2013/0263857 A1 Oct. 10, 2013

(51) Int. Cl.
*A61M 16/00* (2006.01)
*A62B 9/00* (2006.01)
*A62B 27/00* (2006.01)
(Continued)

(52) U.S. Cl.
CPC ............. *A61M 16/00* (2013.01); *A61M 16/044* (2013.01); *A61M 16/0605* (2013.01); *A61M 16/107* (2013.01); *A61M 16/20* (2013.01); *A61M 2016/0021* (2013.01); *A61M 2016/0027* (2013.01); *A61M 2205/15* (2013.01); *A61M 2205/18* (2013.01); *A61M 2205/3355* (2013.01); *A61M 2205/3365* (2013.01);
(Continued)

(58) Field of Classification Search
CPC ............ A61M 16/00; A61M 2205/15; A61M 2205/58–2205/583

USPC ............. 128/202.22, 204.21, 204.23, 205.23, 128/205.25
See application file for complete search history.

(56) References Cited

U.S. PATENT DOCUMENTS

| 4,846,166 A | * | 7/1989 | Willeke | .................... 128/200.24 |
| 5,551,419 A | | 9/1996 | Froehlich et al. | |

(Continued)

FOREIGN PATENT DOCUMENTS

| WO | WO8702898 | 5/1987 |
| WO | WO00037135 | 6/2000 |
| WO | WO2011073814 | 6/2011 |

OTHER PUBLICATIONS

Notification of Transmittal of the International Search Report and the Written Opinion of the International Searching Authority dated Jun. 21, 2013; 10 pages.

*Primary Examiner* — Kristten Matter
(74) *Attorney, Agent, or Firm* — Stetina Brunda Garred & Brucker

(57) ABSTRACT

Indicating fit status of a mask in communication with a respiratory assistance device is disclosed. Upon initiating a therapeutic gas delivery from the respiratory assistance device to the mask, one or more measurements from respective one or more sensors of the respiratory assistance device is received. A leakage value from these measurements is derived, and a mask fit index is assigned. This is based at least upon a correlation of the leakage value to a particular sub-range of predetermined leakage values that corresponds to the mask fit index. The particular sub-range of predetermined leakage values is one among a plurality of sub-ranges, which together comprises an overall mask fit range defined at least by an ideal mask fit region, a loose mask fit region, and a tight mask fit region. A mask fit status based upon the assigned mask fit index is output to an indicator interface.

21 Claims, 5 Drawing Sheets

(51) Int. Cl.
   *A62B 7/00*    (2006.01)
   *G08B 3/00*    (2006.01)
   *G08B 5/00*    (2006.01)
   *F16K 31/02*   (2006.01)
   *A61M 16/06*   (2006.01)
   *A61M 16/10*   (2006.01)
   *A61M 16/04*   (2006.01)
   *A61M 16/20*   (2006.01)

(52) U.S. Cl.
   CPC ... *A61M 2205/3368* (2013.01); *A61M 2205/42* (2013.01); *A61M 2205/502* (2013.01)
   USPC ................................. 128/204.23; 128/202.22

(56) References Cited

U.S. PATENT DOCUMENTS

| | | | |
|---|---|---|---|
| 6,369,838 | B1 | 4/2002 | Wallace et al. |
| 6,425,395 | B1* | 7/2002 | Brewer et al. ............ 128/202.22 |
| 6,546,930 | B1* | 4/2003 | Emerson et al. ......... 128/204.21 |
| 6,675,801 | B2 | 1/2004 | Wallace et al. |
| 8,021,310 | B2 | 9/2011 | Sanborn et al. |
| 2006/0174883 | A1* | 8/2006 | Aylsworth et al. ....... 128/204.21 |
| 2011/0128008 | A1 | 6/2011 | Carter |
| 2011/0307194 | A1 | 12/2011 | Wickham et al. |

* cited by examiner

MECHANICAL VENTILATION MASK FIT STATUS INDICATION

CROSS-REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

1. Field of the Invention

The present disclosure relates generally to the treatment of respiratory and cardiovascular conditions, and more particularly, to methods and systems for indicating mask fit status in mechanical ventilation, such as continuous positive airway pressure (CPAP) therapy.

2. Description of the Related Art

Mechanical ventilators comprise medical devices that either perform or supplement breathing for patients. Early ventilators, such as the "iron lung," created negative pressure around the patient's chest to cause a flow of ambient air through the patient's nose and/or mouth into the lungs. However, the vast majority of contemporary ventilators instead use positive pressure to deliver gas to the patient's lungs via a patient circuit between the ventilator and the patient. The patient circuit typically consists of one or two large bore tubes (e.g., 22 mm inner diameter for adults; 15 mm inner diameter for pediatrics) that interface to the ventilator on one end and a patient mask on the other end.

Ventilators may support either a single limb or a dual limb patient circuit. Single limb patient circuits are typically utilized for less acute clinical requirements such as the treatment of obstructive sleep apnea or respiratory insufficiency. In further detail, the single limb patient circuit, as its nomenclature suggests, involves gas flow from the ventilator to the patient and patient mask over a single conduit. The patient inspires fresh gas from the patient circuit, and expires carbon dioxide-enriched gas that is purged from the system through vent holes in the mask or exhalation ports in the tubing.

One particular application of ventilator devices is in the treatment of obstructive sleep apnea (OSA) syndrome, where the patient's upper airway narrows or collapses during sleep. There are repetitive pauses in breathing that may extend in duration up to half a minute. Although some degree of apnea is considered normal, in more severe cases, daytime sleepiness and fatigue may result as a consequence of reduced blood oxygen saturation, as well as constant interruptions to sleep cycles. In order to retain the patient's airway and ensure normal, uninterrupted breathing during sleep, continuous positive airway pressure (CPAP) therapy may be prescribed.

Generally, CPAP involves the application of positive pressure to open the patient's airway to prevent its collapse, as would otherwise occur during apnea. In a basic implementation, CPAP therapy applies a constant pressure that is not tied to the patient's normal breathing cycle. The positive airway pressure is desired in the inspiratory phase when the pressure differences between the lungs and the nose contribute to the collapse of the intermediate airway. Various improvements have been developed that reduce positive pressure flow to the patient during the expiratory phase, thereby reducing resistance to the patient's breathing efforts and patient discomfort. Further refinements that recognize the minimal flow and pressure toward the end of the patient's expiratory phase and responsively reduce the delivery of positive pressure have also been contemplated.

Typically, CPAP ventilator devices are comprised of a blower unit and a patient mask that are connected to each other over a gas flow conduit. The blower unit delivers the appropriate level of therapeutic gas flow to the patient as initially set by the clinician, and is further regulated based upon a function of the patient's breathing cycle. In order to maintain this gas flow, leakage from within the patient circuit, i.e., the pneumatic circuit comprised of the blower unit, the conduit, the patient mask, and the patient airway, must be maintained within acceptable minimum and maximum threshold levels. It will be recognized that if there little to no leakage, it may be indicative of the mask being placed on the patient too tightly, leading to discomfort and potential skin irritation. On the other hand, if there is too much leakage, the increased flow of gas may cause airway dryness, and cause airflow to be directed toward the eyes to cause dry eyes, and result in additional noise, all contributing to further patient discomfort. Furthermore, the leak may divert too much of the airflow to maintain the prescribed amount of positive pressure in the patient airway.

As a result of the need for increased gas flow, power consumption would increase. From a broader, environmental consciousness standpoint, increased power consumption is problematic, particularly for an apparatus that is run every day for approximately eight hours at a time, indefinitely. Seemingly minor instantaneous power surges over a single breathing cycle may each add up to substantial increases in overall power draw. Unnecessary power consumption is particularly problematic where the power source is limited, such as in battery-powered units.

In general, existing CPAP apparatuses regulate the delivery of therapeutic gas to the patient based upon flow volume measurements and/or calculations. With the flow value being available as a result thereof, leak indication may simply involve the display of those flow values, or the display of calculated percentages of flow values. The patient or the clinician therefore becomes responsible for evaluating the leakage status without additional meaningful assistance.

Accordingly, there is a need in the art for improved methods and systems for mechanical ventilation mask fit status indication, particularly in apparatuses utilized in continuous positive airway pressure (CPAP) therapy with dual pressure sensors at a source and on a ventilation mask. Furthermore, there is a need in the art for improved user interfaces for mask fit status indication.

BRIEF SUMMARY OF THE INVENTION

The present disclosure contemplates various mask fitment indicators utilized in connection with CPAP respiratory assistance devices, so that patients can better adjust the positioning of the mask for optimum comfort. One embodiment contemplates a method for indicating fit status of a mask in pneumatic communication with the respiratory assistance device. The method may include initiating a therapeutic gas delivery from the respiratory assistance device to the mask. Furthermore, the method may include a step of receiving one or more measurements associated with the therapeutic gas delivery. These measurements may be from respective one or more sensors of the respiratory assistance device. There may also be a step of deriving a leakage value from the received one or more measurements that are associated with the therapeutic gas delivery. The method may further include assigning a mask fit index based at least upon a correlation of the leakage value to a particular sub-range of predetermined leakage values that corresponds to the mask fit index. The particular sub-range of predetermined leakage values may be one among a plurality of the sub-ranges, which together comprises an overall mask fit range. This overall mask fit range may be defined at least by an ideal mask fit region, a loose mask fit region, and a tight mask fit region. There may also be a step of generating an output of a mask fit status to an indicator interface. The mask fit status may be based upon the assigned mask fit index. Certain other embodiments of the present disclosure contemplate a computer-readable program storage medium that tangibly embodies one or more programs of instructions executable by a data processing device to perform the foregoing method.

Another embodiment of the present disclosure contemplates a respiratory assistance device. It may have an indicator display interface, as well as a therapeutic gas flow source in pneumatic communication with a patient over a passageway. There may further be at least one sensor that is in line with the passageway for reading gas delivery measurements therefrom. There device may also include a fit indication controller that can be connected to the at least one sensor and the indicator display interface. A leakage value that may be derived from the gas delivery measurements can be correlated by the fit indication controller to a particular sub-range of predetermined leakage value that corresponds to a particular mask fit index. The mask fit index may then be output to the indicator display interface as a mask fit status. The particular sub-range of predetermined leakage values may be among a plurality of the sub-ranges which together comprises an overall mask fit range.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which like numbers refer to like parts throughout, and in which.

Common reference numerals are used throughout the drawings and the detailed description to indicate the same elements.

DETAILED DESCRIPTION OF THE INVENTION

The detailed description set forth below in connection with the appended drawings is intended as a description of the several presently contemplated embodiments of mechanical ventilation mask fit status indication for a continuous positive airway pressure (CPAP) therapy system. Generally, the system delivers breathing gas to a patient for the treatment of obstructive sleep apnea (OSA) and other cardio-pulmonary conditions, and selectively augments and relieves pressure throughout the breathing cycle. This description is not intended to represent the only form in which the disclosed invention may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
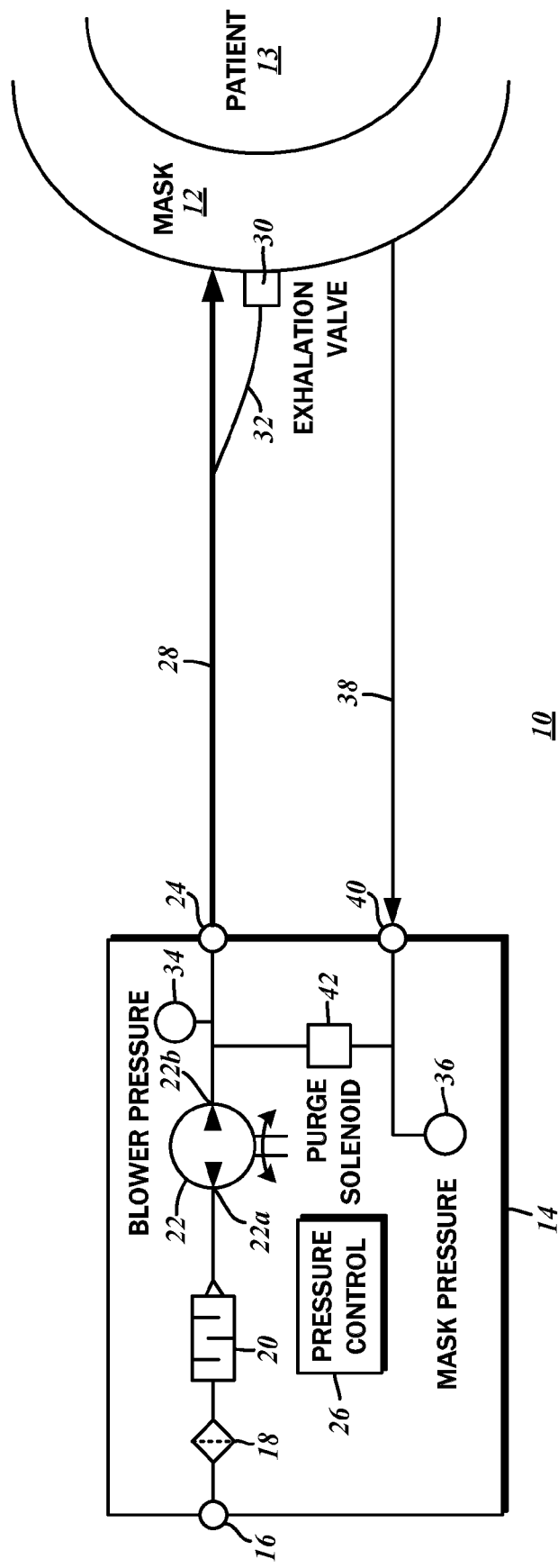
FIG. 1 is a block diagram showing the various components of a CPAP apparatus in accordance with various embodiments of the present disclosure including a typical ventilation unit, a patient ventilation mask, and gas passage conduits.

The block diagram of FIG. 1 illustrates an exemplary CPAP system 10 in which various embodiments of the presently contemplated mask fit status indication may be implemented. There is a patient ventilation interface or mask 12, and a ventilation unit 14. The following disclosure will make reference to the patient ventilation interface and the mask 12 interchangeably. It is understood to be an apparatus such as a full-face mask or a nasal pillows mask that can be placed in direct gas flow communication with the upper respiratory tract, i.e., the nasal cavity and/or the oral cavity, of a patient 13. One possible mask 12 is disclosed in U.S. patent application Ser. No. 13/411,348 entitled VENTILATION MASK WITH INTEGRATED PILOTED EXHALATION VALVE filed Mar. 2, 2012, now issued U.S. Pat. No. 8,844,533, and U.S. patent application Ser. No. 13/411,407 entitled VENTILATION MASK WITH INTEGRATED PILOTED EXHALATION VALVE filed Mar. 2, 2012, now issued U.S. Pat. No. 8,839,791, the disclosures of which are hereby incorporated by reference in their entireties herein. It will be appreciated that other apparatuses that so interface the respiratory tract of the patient 13 to the ventilation unit 14 may be substituted without departing from the scope of the present disclosure.

The ventilation unit 14 generates a flow of breathing gas that is delivered to the patient via the patient ventilation interface 12. The breathing gas may be ambient air a combination of ambient air enriched with oxygen, or any other suitable mixture of gas appropriate for treating the patient. Those having ordinary skill in the art will recognize the variety of options for mixing breathing gasses before delivery to the patient. In further detail, the ventilation unit 14 includes a first inlet port 16, through which ambient air is drawn. The first inlet port 16 is in communication with an inlet filter 18 that removes particulates and other contaminants from the breathing gas that is ultimately delivered to the patient. Optionally, in line with the inlet filter 18 is a sound suppressor 20 that reduces the sound of gas flow through the ventilation unit 14.

The force needed for drawing the ambient air through the first inlet port 16, the inlet filter 18, and the sound suppressor 20 is provided by a centrifugal fan or blower 22. In this regard, the blower has a blower inlet port 22a coupled to the sound suppressor 20, and a blower outlet port 22b that is in gas flow communication with an outlet port 24 of the ventilation unit 14. It will be recognized that any suitable blower 22 capable of generating the gas flow and pressure suitable for CPAP treatment in accordance with the present disclosure may be utilized. The blower 22 is driven electrically and its actuation is governed by a programmable pressure controller 26, which implements the various methods of CPAP treatment contemplated by co-pending U.S. patent application Ser. No. 13/411, 257 entitled DUAL PRESSURE SENSOR CONTINUOUS POSITIVE AIRWAY PRESSURE (CPAP) THERAPY, filed Mar. 2, 2012, the disclosure of which is hereby incorporated by reference in its entirety herein.

The flow of breathing gas that is output from the blower 22 is passed through the outlet port 24 to a gas conduit 28 that is in coupled to the aforementioned patient ventilation interface or mask 12. The gas conduit 28 is understood to be a plastic tube having a predetermined inner diameter such as 22 mm or smaller, though any other conduit of suitable material and construction may be utilized. The mask 12 in accordance with various embodiments of the present disclosure also includes a piloted exhalation valve 30 that is selectively actuated depending on the pressure differential between the patient ventilation interface 12 and the ventilation unit 14. The exhalation valve 30 is connected to a pilot line 32 that branches from the gas conduit 28. A pressure difference is generated between the patient ventilation interface and the exhalation valve, such that it is closed during inspiration and opened during expiration.

In order to ascertain such pressure differentials, the presently contemplated CPAP system 10 includes dual pressure sensors, including a device or blower pressure sensor 34 and a mask pressure sensor 36. The blower pressure sensor 34 is disposed within the ventilation unit 14, and monitors the pressure at the blower outlet port 22b. The mask pressure sensor 36 is also physically disposed within the ventilation unit 14, but is in direct gas flow communication with the mask or patient ventilation interface 12 over a pressure sensor line 38 that is connected to a second inlet port 40. When the ventilation unit 14 is operating, gas pressure within the pressure sensor line 38 as well as the gas conduit 28 may be connected to deliver a purge flow to clear line 38. This can be done through a purge solenoid 42 connected to both. The purge can be continuous or intermittent according to the patient's breathing phase or pressure difference between the blower pressure and the mask pressure.

Figure 2:
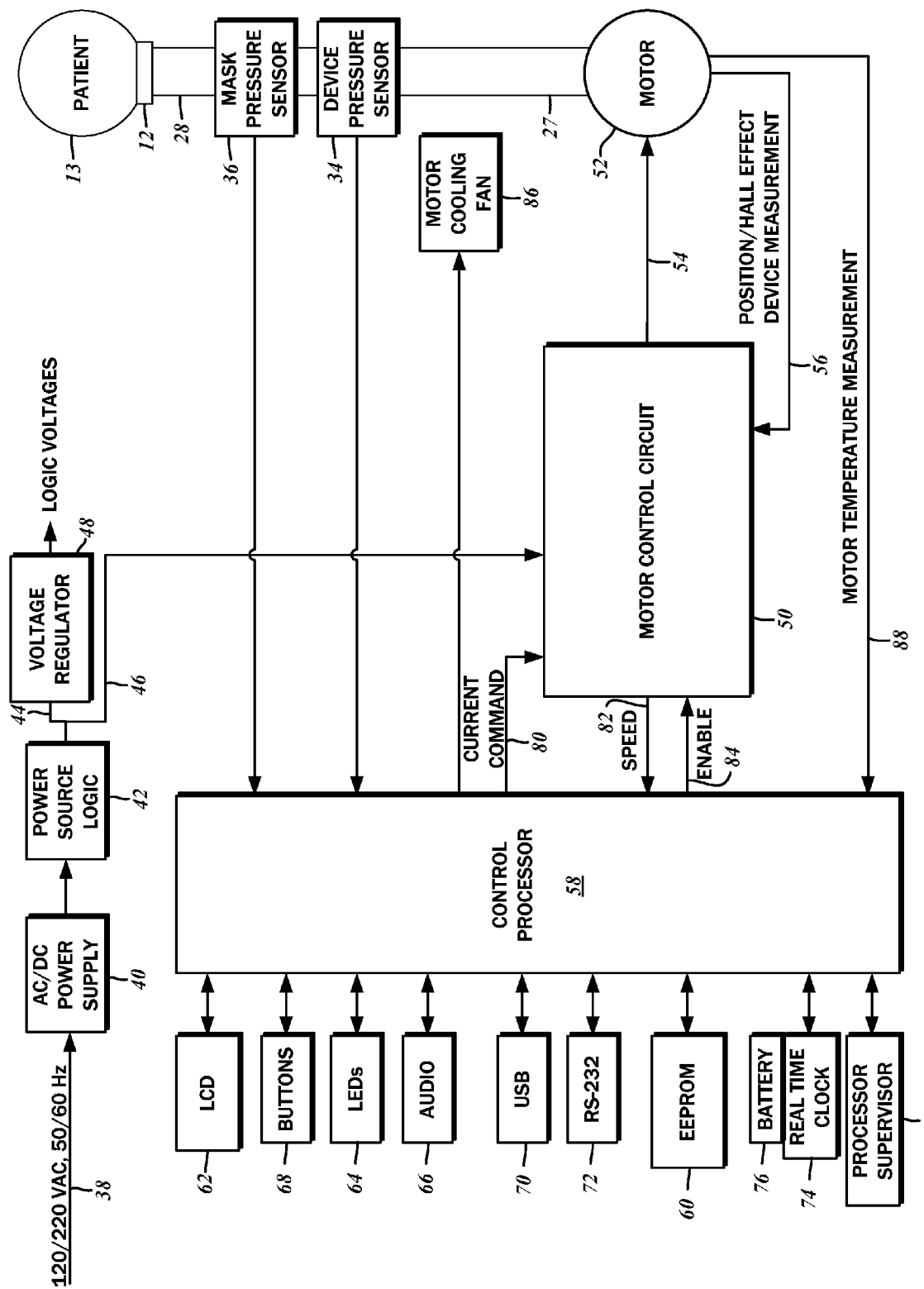
FIG. 2 is a block diagram illustrating the electrical components of the ventilation unit.

The block diagram of FIG. 2 illustrates the various electrical components of one typical embodiment of the ventilation unit 14. Power for the ventilation unit 14 may be provided from a conventional household electricity supply of either 120V or 220V alternating current (AC), at 50 Hz or 60 Hz. The block diagram denotes this supply as a power source 38. A power supply 40 is connected to the power source 38, and as will be recognized by those having ordinary skill in the art, the power signal is variously rectified, filtered, and stepped down to a direct current (DC) voltage. In accordance with one embodiment of the present disclosure, the DC voltage source is 24 V. It is understood that the blower 22 utilizes a higher DC voltage than control logic devices, and thus the power supply 40 is connected to a power source logic 42. A first output 44 of the power source logic 42 is connected to an integrated circuit voltage regulator 48 that steps down the DC voltage to the logic device level of 5V. A second output 46 of the power source logic 42 is the existing high DC voltage directly from the power supply 40, and is connected to a motor control circuit 50.

The blower 22 is comprised of several electrical components, including a motor 52 and the aforementioned motor control circuit 50. In accordance with one embodiment, the motor 52 is a brushless DC or electrically commutated motor. It will be recognized that the speed of rotation of the motor 52 is based upon input logic signals provided to the motor control circuit 50, which drives electrical current through its windings that induce magnetic fields that translate to rotational motion of the attached rotor. A fan coupled to the rotor thus rotates and generates a flow of air through an internal conduit 27. The internal conduit 27 is coupled to the outlet port 24, which is coupled to the gas conduit 28. As described above, the device pressure sensor 34 and the mask pressure sensor 36 are connected to the pneumatic circuit between the motor 52 and the patient 13.

The motor control circuit 50 has a motor drive output 54 that is connected to the motor 52. The position of the motor 52 is detected by a Hall-effect sensor that is incorporated into the motor 52. An output voltage 56 from the Hall-effect sensor is fed back to the motor control circuit 50, which ensures that the actual position corresponds to the intended or commanded position.

The pressure controller 26 and its functionality may be implemented with a programmable integrated circuit device such as a microcontroller or control processor 58. Broadly, the control processor 58 receives certain inputs, and based upon those inputs, generates certain outputs. The specific operations that are performed on the inputs may be programmed as instructions that are executed by the control processor 58. In this regard, the control processor 58 may include an arithmetic/logic unit (ALU), various registers, and input/output ports. Although external memory such as EEPROM (electrically erasable/programmable read only memory) 60 may be connected to the control processor 58 for permanent storage and retrieval of program instructions, there may also be an internal random access memory (RAM). One embodiment contemplates the use of an Intel 8081 instruction set/architecture, though any other suitable instruction set or processor architecture may be substituted. As indicated above, the control processor 58 is powered by a low voltage DC supply from the voltage regulator 48.

Several output devices are envisioned for the ventilation unit 14. In order to set the operational parameters of the ventilation unit, and to initiate or terminate certain functions, a graphical user interface is provided. Such graphical user interface is generated on a display screen 62, which may be of a liquid crystal display (LCD) type. Any type of graphic may be shown on the display screen 62, though for more specific indicators, a simple light emitting diode (LED) device 64 may be utilized. It will be recognized that alarm conditions, power status, and the like may be indicated with the LED device 64. As will be discussed in further detail below, an array of LED devices 100 may be used to indicate mask fit status to the user. Audible outputs may also be produced with audio transducers 66 that are likewise connected to the control processor 58. Among the contemplated outputs that may be generated on the audio transducer 66 include simple beeps and alarms, as well as sophisticated voice prompts that provide information and instructions.

An operator may interact with the graphical user interface through different input devices such as buttons 68 that are connected to the input ports of the control processor 58. It is understood that the audio transducer 66 may also accept sound input in the form of voice commands, the processing of which is performed may be performed by the control processor 58. Similarly, the display screen 62 may be incorporated with touch sensors, and may also function as an input device that allows an operator to interact with the graphical user interface displayed thereon.

Several modalities for connecting to and communicating with other data processing devices such as general-purpose computers are also contemplated. Accordingly, the control processor 58 may be connected to a universal serial bus (USB) controller 70. For more basic communications, there may be a serial RS-232 transceiver 72. Through these data communications modalities, the configuration options of the ventilation unit 14 may be set, operating profiles may be downloaded, and so forth. Notwithstanding the specific reference to USB and RS-232 communications modalities, any other communications modality including wireless systems may be substituted without departing from the present disclosure.

The functions of the ventilation unit 14 depend on proper synchronization, and so the control processor 58 is connected to a real time clock 74 that maintains a common clock cycle. Although a primary feature of the real time clock 74 is to maintain synchrony at a processor cycle level, longer term time data is also maintained. In order to retain such time data, the real time clock 74 may be powered independently of the primary power source 38, and there is accordingly a battery backup 76. Under heavy processing loads or unexpected program conditions, the control processor 58 may become unable to execute critical programmed steps in real-time. Thus, the control processor 58 may include a processor supervisor 78 that invokes a program execution break upon detecting such conditions. Typically, this is implemented as a step of clearing a memory variable periodically, and when that step is unable to take place because instruction execution is frozen or otherwise delayed, the processor supervisor 78 may cause a predetermined routine to be executed.

As indicated above, the motor 52 is driven by the motor control circuit 50, which generates different outputs depending on signals received from the control processor 58. The signal to drive the motor 52 is generated on a current command line 80. For control processing on a broader level, feedback from the blower 22 is utilized, and in the specific form of a speed or current measurement input 82 from the motor control circuit 50. Furthermore, as detailed below, pressure readings at the blower 22 and the patient 13 are utilized to reach control decisions. Accordingly, the device pressure sensor 34 and the mask pressure sensor 36 are both connected to the control processor 58. The blower 22 is activated and deactivated via a motor enable line 84. To ensure that the temperature of the motor 52 remains within operational parameters, a motor cooling fan 86 may be driven directly by the control processor 58. In some embodiments, there may be additional control circuitry that isolates the power source of the motor cooling fan 86 from the control processor 58. The decision to activate and deactivate the motor cooling fan 86 may be made in response to temperature readings from the motor 52, and so there is a motor temperature reading 88 passed to the control processor 58.

It is understood that over a typical breathing cycle, the pressure at the blower 22 and the pressure at the patient mask 12 vary depending upon whether the patient is in an inspiratory phase or an expiratory phase. The pressure at the blower 22 increases or is elevated during inspiration, while during expiration, it decreases or is depressed. The pressure the patient mask 12 exhibits an opposite response, where it increases or is elevated during expiration, and decreases or is depressed during inspiration. The following discussion will refer to the pressure at the blower 22 as $P_{Blower}$, with the pressure at time t being referred to as $P_{Blower}(t)$, and the pressure at the patient mask 12 as $P_{Mask}$, with the pressure at time t likewise being referred to as $P_{Mask}(t)$. As absolute measurements, $P_{Blower}$ is significantly higher than $P_{Mask}$, and the two values are generally reciprocal—when $P_{Mask}$ peaks, $P_{Blower}$ is at its lowest, and vice versa. Reference to such terms as mask pressure, blower pressure, or the use of the term mask or blower to modify any other term is for purposes of convenience only and not of limitation. For instance, mask pressure is understood to refer to the pressure in the patient ventilation interface or mask 12, while blower pressure refers to the pressure at the output of the blower 22.

Figure 3:
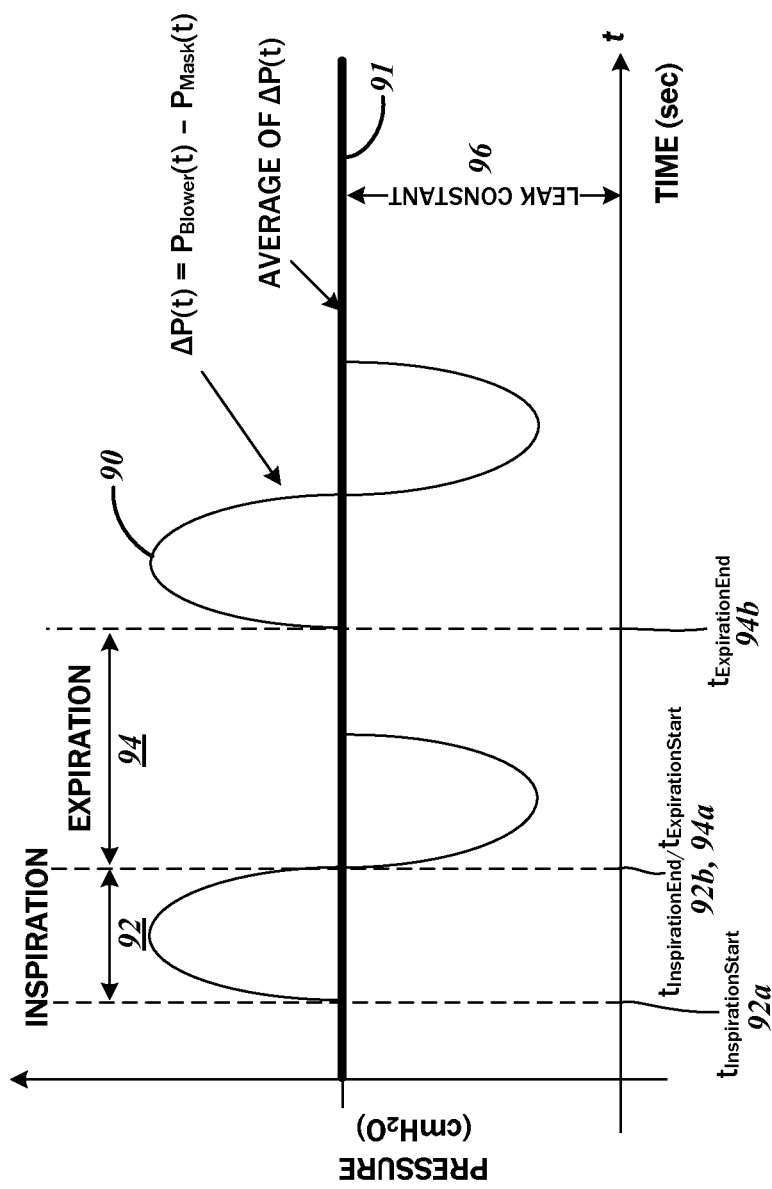
FIG. 3 is a pressure diagram graphically illustrating pressure differences (ΔP) at the blower and the patient mask over typical breathing cycles.

Various embodiments of the present disclosure contemplate the calculation of pressure differences across the patient breathing cycle between the blower 22 and the mask 12, hereinafter referred to as $\Delta P$. The pressure diagram of FIG. 3 shows, in a plot 90, the calculated pressure difference $\Delta P$. The average $\Delta P$ across the breathing cycle is represented as a centerline 91. The region of the plot 90 that is positive is understood to define an inspiration phase 90 that begins at a time $t_{InspirationStart}$ 92a, gradually increasing to a peak difference, and decreasing to a time $t_{InspirationEnd}$ 92b. Coinciding therewith is the start of an expiration phase 94 at $t_{ExpirationStart}$ 94a. The pressure difference $\Delta P$ decreases to a minimum and increases again, after which point remains constant for a period of time and ends at $t_{ExpirationEnd}$ 94b. It is understood that the average $\Delta P$ over a given breathing cycle is also representative of the amount of leakage from the CPAP system 10. Thus, the greater the average $\Delta P$, the greater is the leakage, and the lower the average $\Delta P$, the lesser is the leakage.

Figure 4:
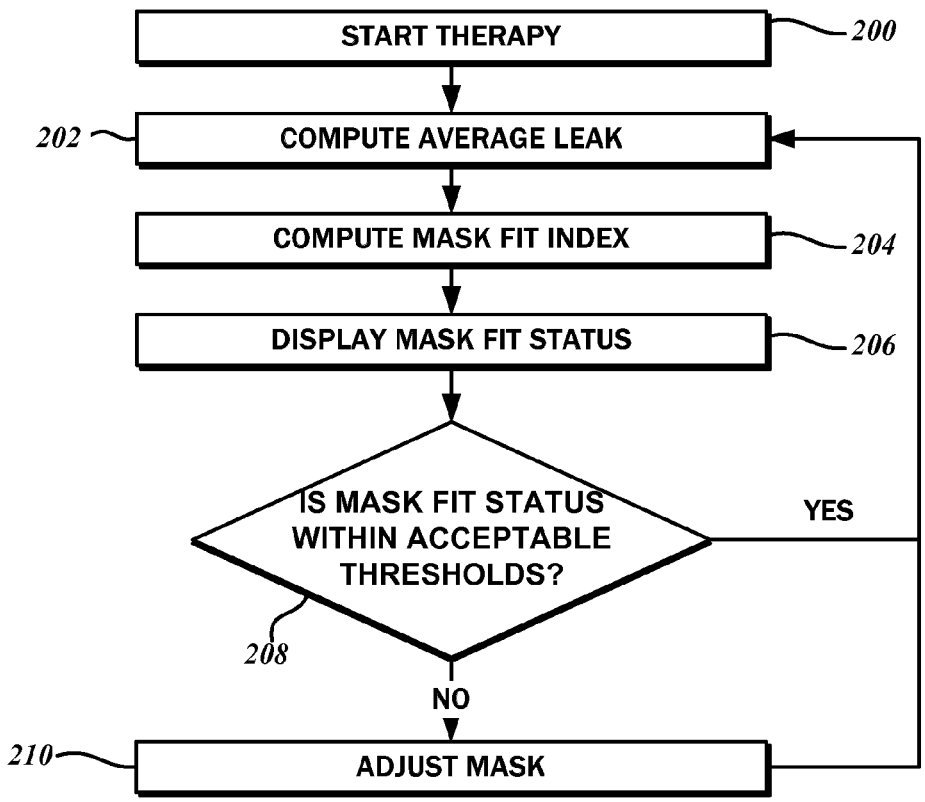
FIG. 4 is a flowchart depicting one method for processing and indicating mask fit.

In accordance with one contemplated embodiment of the mask fit status indication, the amount of leakage corresponding to the leak constant 96 can be utilized for this end. The flowchart of FIG. 4 illustrates a general method of mechanical ventilation mask fit status indication that may begin with a step 200 of initiating the CPAP therapy or ventilation. Thereafter, the method continues with a step 202 of computing average mask leak. As indicated above, the average pressure difference $\Delta P$ between the blower 22 and the mask 12 over one or more breathing cycles corresponds to the leak constant.

Figure 5:
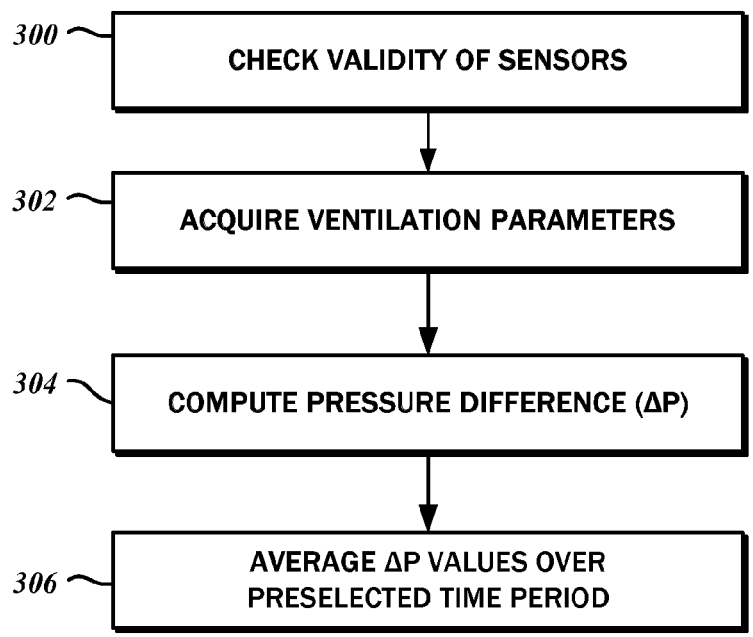
FIG. 5 is a flowchart depicting a method for computing average leak in accordance with one embodiment of the present disclosure.

With reference to the flowchart of FIG. 5, there is additionally contemplated a method for calculating mask leakage. This method begins with a preliminary step 300 of checking the validity of the sensors 34, 36, and a step 302 of acquiring ventilation parameters. The method, and these steps as well as the other following steps, may be implemented as pre-programmed instructions executed by the control processor 58 and stored in a memory connected to the same. The step 302 involves reading the blower pressure sensor 34 and the mask pressure sensor 36 to take instantaneous readings of $P_{Blower}$ and $P_{Mask}$, respectively.

In a step 304, $\Delta P$ is calculated from the difference between the instantaneous readings of $P_{Blower}$ and $P_{Mask}$. More particularly, $\Delta P$ is understood to equal $P_{Blower} - P_{Mask}$. $\Delta P$ measurements/calculations are made at predefined intervals, and may occur as rapidly as hundreds of times a second. The limitation on the number of $\Delta P$ readings taken is largely dependent on the instruction execution speed limits of the control processor 58, and the other operations being simultaneously handled thereby such as motor control, user interface interaction, and so forth.

The average of each of those $\Delta P$ readings is computed in accordance with a step 306. This may involve measuring and calculating average values over several patient breathing cycles. However, it is also possible to compute the average $\Delta P$ over a single breathing cycle, or over a predefined time period independent of the patient's breathing. Those having ordinary skill in the art will recognize the minimum number of breathing cycles needed to make accurate leakage determinations.

Referring to the flowchart of FIG. 4, after the average leak in any given moment is calculated, the method continues with a step 204 of computing a mask fit index. In accordance with various embodiments of the present disclosure, the mask fit index is understood to be a function of the average leak computed in the foregoing step 202. Furthermore, as a further refinement in computing the mask fit index, other factors such as peak flow, therapeutic airflow volume, and mean airway pressure may also be utilized.

Figure 6:
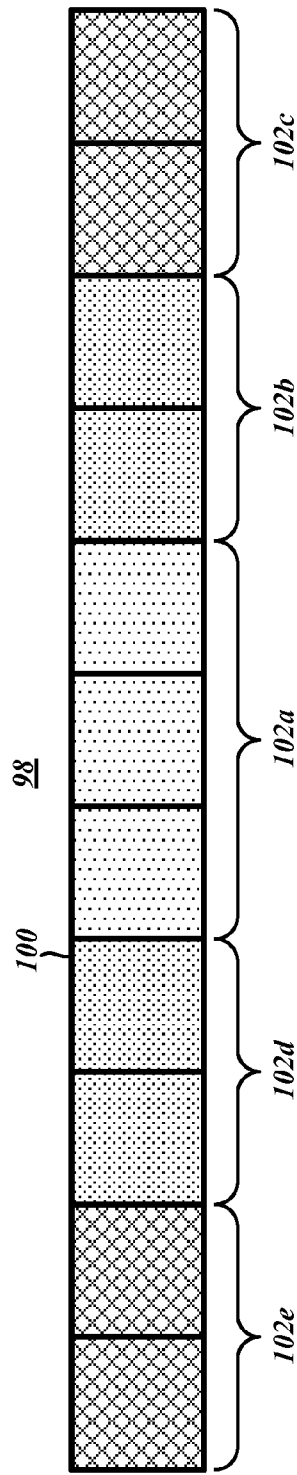
FIG. 6 is a first exemplary interface for indicating mask fit.

Having computed the mask fit index, the method proceeds with a step 206 of displaying a mask fit status. FIG. 6 illustrates a first exemplary indicator interface 98 with a series of indicator elements 100. Each indicator element is understood to be representative of a particular range of values of the mask fit index. A middle section 102*a* corresponds to a proper operating leakage level that requires no further adjustment from the user. A middle right section 102*b* corresponds to a lower leakage level, while a right section 102*c* corresponds to a lowest leakage level. On the other side, a middle left section 102*d* corresponds to a higher leakage level, and a left section 102*e* corresponds a highest leakage level.

Depending on where, exactly, the computed mask fit index falls relative to the limit values for each of the respective indicator elements, particular ones may be activated. Such limit values for each of the indicator elements may be based on absolute minimum and maximum values, various percentages of an ideal mask fit index, standard deviations of an ideal mask fit index, or any other dividing method. An ideal mask fit index is contemplated to be related to the comfort of the patient 13, and under certain circumstances a mask fit index corresponding to greater or lesser leakage may be preferred. Along these lines, it is possible to adjust each of the limit values higher or lower in accordance with the patient's preferences. For example, if the patient 13 prefers a lower leakage level, during one usage session the middle right section 102*b* may be illuminated, but in a subsequent session the mask fit index corresponding thereto may be redefined as the new limit values for the middle section 102*a*. These adjustments may be made by the patient, or determined without user input based on prior usage patterns.

To increase the visual appeal, each specified range of indicators may illuminate with certain predetermined colors. For example, the middle section 102*a* may be illuminated green, while the middle right section 102*b* and the middle left section 102*d* may be illuminated yellow. This may serve as a warning to the user that the mask fit has not been adjusted to the ideal configuration. Additionally, the right section 102*c* and the left section 102*e*, being extreme positions along the indicator elements 100, may be illuminated red to specify that substantial adjustments to the positioning of the mask 12. It will be recognized that any other suitable indicator system that is capable of showing a mask leakage as a certain point along a continuum of minimum and maximum values may be substituted without departing from the scope of the present disclosure. Other contemplated indicators include analog dial-types and alphanumeric characters that indicate "high," "ideal" and "low" leakage levels, among many others.

Figure 7:
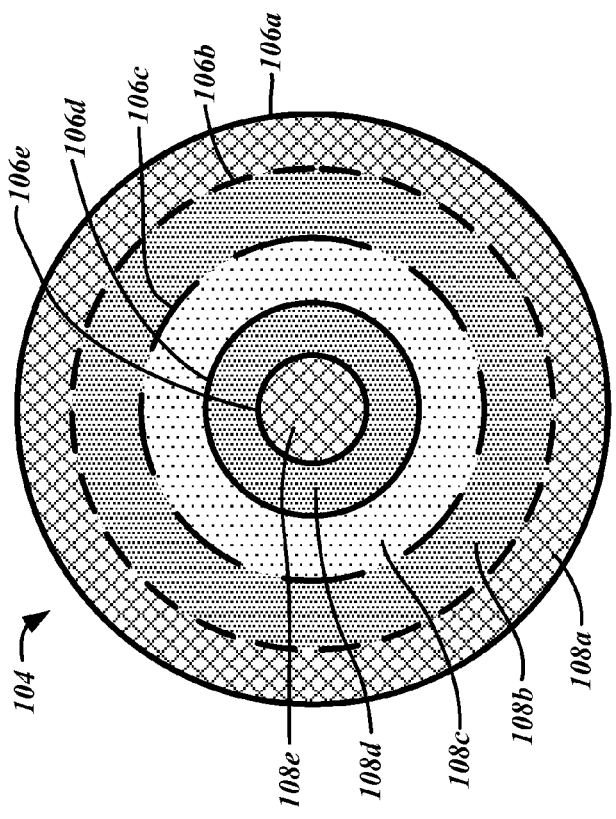
FIG. 7 is a second exemplary interface for indicating mask fit.

FIG. 7 is a second exemplary indicator interface 104 that likewise may be used to indicate mask fit status. It is comprised of a series of concentric rings 106*a*-106*e* that define various regions 108*a*-108*e* bordered by a respective pair of the rings 106. In accordance with one embodiment, the outermost region 108*a* corresponds to the highest leakage level, while the innermost region 108*e* corresponds to the lowest leakage level. A middle region 108*c* may correspond to the proper operating leakage level that does not require adjustment, with the surrounding region 108*d* and 108*e* that correspond to moderately lower and higher leakage levels, respectively. In some embodiments each of the regions 108 may remain illuminated while the region that corresponds to the current mask fit status being illuminated brighter. Alternatively, only the region that corresponds to the current mask fit status may be illuminated. In some cases, the surrounding region or regions of the region that corresponds to the current mask fit status may be illuminated, at a slightly decreased level. Those having ordinary skill in the art will readily ascertain various visualization techniques that could be utilized.

An indicator interface such as that shown in FIG. 6 utilizes a series of indicator elements 100. This may be implemented with LED devices 64 and driven directly by the control processor 58. Alternatively, graphics representative of the indicator elements 100 may be shown through the graphical user interface displayed on the LCD display device 62. If such an effect is desired, analog gauges may also be electrically driven by the control processor 58. Similarly, with regard to the second embodiment of the indicator interface 104 could be implemented as a series of individual LED elements arranged in the manner illustrated, or as graphical elements displayed on a LCD screen.

The indicator interface 98 is updated so long as the CPAP system 10 is activated. In this regard, the method envisions a decision point 208 where it is determined whether the mask fit index is within acceptable thresholds. If it is, in a subsequent iteration, the method resumes with computing an updated average leak. Otherwise, in an optional step performed by a clinician or the patient 13, the positioning and orientation of the mask 12 is adjusted in accordance with a step 210. The method again returns to the step 202 of computing the average leak to repeat the indicator update process as described above.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show details of the present invention with more particularity than is necessary, the description taken with the drawings making apparent to those skilled in the art how the several forms of the present invention may be embodied in practice.

What is claimed is:

1. A method for indicating fit status of a mask in pneumatic communication with a respiratory assistance device, the method comprising:

initiating a therapeutic gas delivery from the respiratory assistance device over a first conduit to the mask;

receiving a first pressure measurement at a blower of the respiratory assistance device, the first pressure measurement being received from a first sensor in line with the first conduit;

receiving a second pressure measurement at the mask, the second pressure measurement being received from a second sensor in pneumatic communication with the mask over a second conduit;

deriving a leakage value from the received first and second pressure measurements;

assigning a mask fit index based at least upon a correlation of the leakage value to a particular sub-range of predetermined leakage values that corresponds to the mask fit index, the particular sub-range of predetermined leakage values being among a plurality of the sub-ranges which together comprises an overall mask fit range defined at least by an ideal mask fit region, a loose mask fit region, and a tight mask fit region; and generating an output of a mask fit status to an indicator interface, the mask fit status being based upon the assigned mask fit index.

2. The method of claim 1, wherein the leakage value is derived from a leak constant that is a function of a pressure difference between the first pressure measurement at the blower and the second pressure measurement at the mask.

3. The method of claim 1, wherein the leakage value is derived from multiple readings over time of the one or more measurements associated with the therapeutic gas delivery.

4. The method of claim 3, wherein the leakage value is derived from an average of the multiple readings over a plurality of breathing cycles.

5. The method of claim 1, wherein the displayed mask fit status corresponds to at least one of the ideal mask fit region, the loose mask fit region, and the tight mask fit region.

6. The method of claim 1, wherein the indicator interface has indicator elements corresponding to each of the plurality of the sub-ranges of predetermined leakage values, at least a first one of the indicator elements corresponding to the particular sub-range of predetermined leakage values of the assigned mask fit index being activated in response to the generated output.

7. The method of claim 6, wherein a second indicator element adjacent to the first one of the indicator elements is activated.

8. The method of claim 1, wherein the predetermined leakage values that define a given sub-range corresponding to the mask fit index are variable.

9. The method of claim 8, further comprising:
adjusting the predetermined leakage values that define the given sub-range corresponding to the mask fit index based upon a patient comfort modifier.

10. The method of claim 9, wherein the patient comfort modifier is a received input from a patient.

11. The method of claim 9, further comprising:
generating the patient comfort modifier from one or more previously assigned values of the mask fit index.

12. The method of claim 1, further comprising:
adjusting the predetermined leakage values that define the given sub-range corresponding to the mask fit index based on one or more previously assigned values of the mask fit index.

13. A respiratory assistance device comprising:
an indicator display interface;
a therapeutic gas flow source in pneumatic communication with a patient ventilation interface over a first conduit, the therapeutic gas flow source including a blower for generating a gas flow in the first conduit;
a first sensor in line with the first conduit for reading gas delivery measurements therefrom, wherein the gas delivery measurements include a first pressure measurement at the blower;
a second sensor in pneumatic communication with the patient ventilation interface over a second conduit for a second pressure measurement at the patient ventilation interface;
a fit indication controller connected to the first sensor, the second sensor and the indicator display interface, a leakage value derived from the first and second pressure measurements being correlated by the fit indication controller to a particular sub-range of predetermined leakage value that corresponds to a particular mask fit index, the mask fit index being output to the indicator display interface as a mask fit status;
wherein the particular sub-range of predetermined leakage values is among a plurality of the sub-ranges which together comprises an overall mask fit range.

14. The respiratory assistance device of claim 13, wherein the overall mask fit range is defined at least by an ideal mask fit region, a loose mask fit region, and a tight mask fit region.

15. The respiratory assistance device of claim 14, wherein the indicator interface has indicator elements corresponding to each of the plurality of the sub-ranges of predetermined leakage values, at least a first one of the indicator elements corresponding to the particular sub-range of predetermined leakage values of the assigned mask fit index being activated in response to the generated output.

16. The respiratory assistance device of claim 13, wherein:
the leakage value is derived from a leak constant that is a function of a pressure difference between the first pressure measurement and the second pressure measurement.

17. The respiratory assistance device of claim 13, further comprising a purge solenoid in pneumatic communication with the first conduit and the second conduit and configured to deliver a purge flow to clear the second conduit.

18. An article of manufacture comprising a non-transitory program storage medium readable by a computer, the medium tangibly embodying one or more programs of instructions executable by the computer to perform a method for indicating fit status of a mask in pneumatic communication with a respiratory assistance device, the method comprising:
initiating a therapeutic gas delivery from the respiratory assistance device over a first conduit to the mask;
receiving a first pressure measurement at a blower of the respiratory assistance device, the first pressure measurement being received from a first sensor in line with the first conduit;
receiving a second pressure measurement at the mask, the second pressure measurement being received from a second sensor in pneumatic communication with the mask over a second conduit;
deriving a leakage value from the received first and second pressure measurements;
assigning a mask fit index based at least upon a correlation of the leakage value to a particular sub-range of predetermined leakage values that corresponds to the mask fit index, the particular sub-range of predetermined leakage values being among a plurality of the sub-ranges which together comprises an overall mask fit range defined at least by an ideal mask fit region, a loose mask fit region, and a tight mask fit region; and
generating an output of a mask fit status to an indicator interface, the mask fit status being based upon the assigned mask fit index.

19. The article of manufacture of claim 18, wherein the indicator interface has indicator elements corresponding to each of the plurality of the sub-ranges of predetermined leakage values, at least a first one of the indicator elements corresponding to the particular sub-range of predetermined leakage values of the assigned mask fit index being activated in response to the generated output.

20. The article of manufacture of claim 18, wherein:
the leakage value is derived from a leak constant that is a function of a pressure difference between the first pressure measurement and the second pressure measurement.

21. A method for indicating fit status of a mask in pneumatic communication with a respiratory assistance device, the method comprising:
initiating a therapeutic gas delivery from the respiratory assistance device to the mask;
receiving one or more measurements associated with the therapeutic gas delivery from one or more sensors of the respiratory assistance device;
deriving a leakage value from the received one or more measurements associated with the therapeutic gas delivery;

assigning a mask fit index based at least upon a correlation of the leakage value to a particular sub-range of predetermined leakage values that corresponds to the mask fit index, wherein the predetermined leakage values that define a given sub-range corresponding to the mask fit index are variable, the particular sub-range of predetermined leakage values being among a plurality of the sub-ranges which together comprises an overall mask fit range defined at least by an ideal mask fit region, a loose mask fit region, and a tight mask fit region;

generating a patient comfort modifier from one or more previously assigned values of the mask fit index;

adjusting the predetermined leakage values that define the given sub-range corresponding to the mask fit index based upon the patient comfort modifier; and generating an output of a mask fit status to an indicator interface, the mask fit status being based upon the assigned mask fit index.

* * * * *